United States Patent
Salzet et al.

(10) Patent No.: US 10,254,275 B2
(45) Date of Patent: Apr. 9, 2019

(54) DEVICE FOR REAL-TIME IN VIVO MOLECULAR ANALYSIS

(71) Applicants: UNIVERSITE DES SCIENCES ET TECHNOLOGIES DE LILLE, Villeneuve d'Ascq (FR); CENTRE NATIONAL DE LA RECHERCHE SCIENTIFIQUE, Paris (FR)

(72) Inventors: Michel Salzet, Bourghelles (FR); Isabelle Fournier, Bourghelles (FR); Cristian Focsa, Wattignies (FR); Michael Ziskind, Lille (FR); Benoit Fatou, Beauvin (FR); Maxence Wisztorski, Chereng (FR)

(73) Assignees: UNIVERSITE DE SCIENCES ET TECHNOLOGIES DE LILLE, Villeneuve d'Ascq (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 11 days.

(21) Appl. No.: 15/512,703

(22) PCT Filed: Sep. 22, 2015

(86) PCT No.: PCT/IB2015/057301
§ 371 (c)(1),
(2) Date: Mar. 20, 2017

(87) PCT Pub. No.: WO2016/046748
PCT Pub. Date: Mar. 31, 2016

(65) Prior Publication Data
US 2017/0285012 A1    Oct. 5, 2017

(30) Foreign Application Priority Data

Sep. 22, 2014 (FR) ..................... 14 58925

(51) Int. Cl.
*G01N 33/50* (2006.01)
*G01N 33/566* (2006.01)
(Continued)

(52) U.S. Cl.
CPC ..... *G01N 33/5091* (2013.01); *A61B 5/14503* (2013.01); *A61B 5/14546* (2013.01);
(Continued)

(58) Field of Classification Search
CPC .. G01N 33/5091; G01N 33/566; A61K 38/00; A61K 49/00; C12N 5/00; C12Q 1/02; A61B 5/00
(Continued)

(56) References Cited

U.S. PATENT DOCUMENTS 6,358,243 B1    3/2002 Esterowitz et al.
7,375,319 B1    5/2008 Willoughby et al.
(Continued)

FOREIGN PATENT DOCUMENTS

DE    4200497 A1    7/1993
WO    2014079802 A2    5/2014

OTHER PUBLICATIONS

Calligaris D. et al., "Mass spectrometry imaging as a tool for surgical decision-making", Journal of Mass Spectrometry, vol. 48, No. 11 pp. 1178-1187 (Jul. 2013).
(Continued)

*Primary Examiner* — Nicole M Ippolito
(74) *Attorney, Agent, or Firm* — Browdy and Neimark, P.L.L.C.

(57) ABSTRACT

The invention relates to a biological material molecular analysis device characterized in that it includes:—a laser (34) optionally using an optical parametric oscillator (OPO), configured to emit a wavelength between 2.5 ym and 12 put, said configured laser (34) being intended to ablate said
(Continued)

biological material by ejecting charged and/or uncharged particles;—a mass spectrometer (31); and—a probe (S, 10) comprising at least one first analysis fiber (A, 14), connected to the laser (34), and a transfer tube (T, 21), connected to the mass spectrometer (31).

23 Claims, 6 Drawing Sheets (51) Int. Cl.
*C12Q 1/02* (2006.01)
*A61B 5/145* (2006.01)
*H01J 49/04* (2006.01)
*A61B 10/02* (2006.01)
*G01N 1/04* (2006.01)
*A61B 5/00* (2006.01)
*A61K 38/00* (2006.01)
*A61K 49/00* (2006.01)
*C12N 5/00* (2006.01)

(52) U.S. Cl.
CPC .............. *A61B 10/02* (2013.01); *C12Q 1/02* (2013.01); *G01N 33/566* (2013.01); *H01J 49/0463* (2013.01); *A61B 5/00* (2013.01); *A61K 38/00* (2013.01); *A61K 49/00* (2013.01); *C12N 5/00* (2013.01); *G01N 2001/045* (2013.01)

(58) Field of Classification Search
USPC ................................ 250/281, 282, 283, 288
See application file for complete search history.

(56) References Cited

U.S. PATENT DOCUMENTS

| 7,910,881 B2 | 3/2011 | Nikolaev et al. |
| 2002/0121596 A1 | 9/2002 | Laiko et al. |
| 2008/0035844 A1 | 2/2008 | Sakata et al. |
| 2010/0012831 A1 | 1/2010 | Vertes et al. |
| 2011/0215233 A1* | 9/2011 | Vertes .................... H01J 49/26 250/251 |
| 2011/0248164 A1* | 10/2011 | Straw .................... H01J 37/226 250/307 |
| 2012/0156712 A1 | 6/2012 | Takats et al. |

OTHER PUBLICATIONS

Chein-Hsun et al., "Development of a mass spectrometry sampling probe for chemical analysis in surgical and endoscopic procedures", Analytical chemistry, pp. 11843-11850, vol. 85 No. 24, (Aug. 2013).
Nemes et al., "Laser Ablation Electrospray Ionization for Atmospheric Pressure, in Vivo, and Imaging Mass Spectrometry", Analytical chemistry, pp. 8098-8106, vol. 79 No. 21 (Sep. 2007).
Park et al.,"Infrared Laser Ablation Sample Transfer for MALDI and Electrospray", Journal of the American Society for Mass Spectrometry, pp. 1352-1362 , vol. 22 No. 8 (May 2011).
Schafer et al., "In Situ, Real-Time Identification of Biological Tissues by Ultraviolet and Infrared Laser Desorption Ionization Mass Spectrometry", Anal. Chem., pp. 1632-1640, vol. 83, (Feb. 2011).

* cited by examiner

DEVICE FOR REAL-TIME IN VIVO MOLECULAR ANALYSIS

The present invention relates to a device for in vivo molecular analysis in real time.

The field of the invention is that of the analysis of cells of a living organism.

Early diagnosis of pathologies is a crucial step for surgeons and clinicians. The diagnostics should lead to making a clear decision as rapidly as possible on the physiopathological condition of the patient (human or animal). This step should be carried out within a short lapse of time and this with a minimum of damages for the patient and without imposing on him/her additional complications.

For 25 years, several non-invasive diagnostic tools have been developed, notably magnetic resonance imaging, the scanner, Positron Emission Tomography (PET) or sinography. These techniques are effective for observing, localizing and determining the size of abnormal regions from a tissue point of view like cancer regions. Certain of these techniques may even give more specific information like the production of new blood vessels inside these regions (neoangiogenesis) or cell catabolism.

However, none of these techniques has the capacity of giving information on the molecular contents of the relevant region. This information is notably absent for posing a diagnostic or even a prognose of the pathology. Such a widely used strategy within the hospital is to proceed with excision of tissues (biopsy) in the abnormal region and then carrying out ex-vivo analysis on the tissue with different techniques and notably histological techniques (e.g. anatomopathological examination) for seeking morphological, cell, tissue or molecular characteristics. Within the scope of cancers, such practice gives the possibility of confirming the presence of malign tumors and to obtain their histological classification (type, grade). Other more targeted techniques may be applied for obtaining a diagnostic such as immunohistochemistry (IHC) or PCR techniques in order to search for specific markers of the pathology or particular mutations.

Although this strategy is widely used, it may prove to be long, leaving during this period the patient in the operating room while waiting for his/her diagnostic. Therefore there is a real interest for the development of techniques allowing the collection of in-vivo molecular information. The sought device should give the possibility of obtaining this in-vivo information but also in real time during the time of presence in the operating room.

From among the techniques which may give the possibility of obtaining in-vivo molecular information, there is a need for spectroscopic techniques. Raman, IR or fluorescence spectroscopies are techniques meeting these criteria. However, these techniques have certain drawbacks which are either the requirement of using a tracer for viewing the region of interest, or of collecting complex profiles (i.e. each molecule has in the analyzed region gives a complex spectrum and the spectrum of the analyzed cell region is a superposition of the whole of the spectra of the molecules making up the region) not always giving the possibility of observing molecular variations between a normal and pathological area and requiring the use of extremely complex statistical processing operations.

On the other hand, another spectroscopic method, mass spectrometry, may meet this need for a rapid diagnostic in-vivo in real time. Mass spectrometry is a technique based on the measurement of the molecular weight of the species. Conventionally, the mass measurement is carried out according to the diagram, generation of ions in a gas phase from the sample (in-vitro) by the source of producing ions of the instrument, separation of the formed ions according to the ratio m/z in the analyzer portion and then detection of the ion current. The analyzed samples may be solid, liquid or gaseous. However, the source of ions used will be adapted to the condition in which is found the sample. From complex mixtures, mass spectrometry provides the advantage of allowing observation of a signal for each species since the latter are separated according to m/z except if the compounds have the same raw formula or if the performances of the instrument are insufficient. Historically, mass spectrometry leads to the arrival of different technologies for sources of ion production and analyzers, the sources and analyzers being able to be combined with each other in different ways allowing the creation of instruments with characteristics defined in terms of compounds which may be analyzed, of sample condition, of instrumental performances. More recently, mass spectrometry techniques have evolved so as to give the possibility of passing from the analysis of in-vitro extracts to the analysis of organisms or organism portions ex-vivo. The development of these techniques has contributed to the arrival of a new field of research entitled Imaging by Mass Spectrometry. Presently, the sources for producing ions the most currently used since compatible in this field are the sources of so called Secondary Ion Mass Spectrometry (SIMS), Laser Desorption Ionization (LDI) sources, the Matrix Assisted Laser Desorption/Ionization (MALDI) sources, the Desorption Electrospray Ionization sources (DESI) and the Laser Ablation-Inductively Coupled Plasma (LA-ICP). These technologies as such allow analysis of organisms or organism portions ex-vivo for which they give the possibility of molecular characterization but they cannot be used in-vivo on living organisms.

Indeed, in the case of DESI "for Desorption Electrospray Ionization", a jet of charged droplets of solvent produced by an electro-nebulization process is directed onto the surface of the sample. The droplets will rebound at the surface of the sample with a process for capturing surface molecules during the interaction phase of the droplets with the surface. The molecules are sucked up by a capillary intended for entering the mass spectrometer. The DESI source has proven its capacities for multiple biological samples like tissues or organs. This is illustrated in the article of Calligaris D et al., 2013, J Mass Spectrometry, 48 (II), 1178-87 wherein DESI is combined with conventional in-vivo imaging. An instrumental modification was carried out for attempting the use of DESI in vivo: Chen CH et al, 2013, Anal. Chem 85(24), 11843-50. In this case, a pressurized solvent jet is directed onto the tissue. The jet is positioned inside a transfer tube giving the possibility of ensuring the transport of the charged molecules generated by the jet towards the mass spectrometer. In spite of its use in-vivo, this instrument requires a contact with the area to be analyzed. The analysis of the surface in a continuous way may induce contamination effect for characterization of biological tissues.

In order to circumvent this problem, a solution is laser ablation as a desorption method: Nemes P, Vertes A, 2007 Anal. Chem., 79(21), 8098-106—Park SG, Murray K K, 2011 J. Am. Soc. Mass Spectrom. 22(8), 1352-62. A laser ablation technique followed by capture of the ablated molecules by an electro-nebulization solvent jet, a technique known under the acronym of LAESI (for "Laser Ablation ElectroSpray Ionization") was introduced by the same team and the team of Pr. K. Murray in the same year (2007). Ablation is accomplished with a pulsed laser emitting in the infrared domain. The ablated molecules are ionized with an electrospray jet and transferred towards the inlet of the mass spectrometer. The advantage consists in the excitation of abundant biological molecules like water with a low space resolution. This technique was already used for living organisms. This technique is difficult to miniaturize and requires the use of a solvent with the drawbacks which this includes within a focus for in-vivo use.

The invasive techniques will be left aside in the case of the present device and notably those resorting to a bistoury regardless of its nature (manual, electrical, . . . ).

Document US 2010/0012831 teaches an ex-vivo 3D molecular imaging method based on the LAESI technique. In the LAESI method an infrared laser is used for ablating the molecules. The ablated molecules are captured by a jet of charged organic solvent droplets produced by ionization by Electrospray (ESI) and then brought towards the mass analyzer via an interface using electric fields. Here, the ablated material, in order to be analyzed, should be captured by a jet of organic solvent droplets, which is not compatible with the in-vivo use, as well as the application of an electric field. The devices used for the LAESI technique are not compatible because of their structure for in-vivo use since they are essentially designed for ex-vivo use.

Document U.S. Pat. No. 7,910,881 is related to the preceding document and has an ex-vivo analysis method based on the LADC (Laser Ablation Droplet Capture) technique. Here the sample is desorbed from the surface and then captured in a solvent placed in a capillary above the ablation point. The sample to be analyzed is therefore dissolved in a solvent before being transferred to the mass spectrometer. A real time analysis cannot be contemplated with this device because of the time taken by the sample to arrive to the analyzer and possible material losses during the transfer.

Document US 2012/0156712 proposes a system for analyzing tissues in-vivo in real time. The ablation of the tissue to be analyzed is accomplished by means of an electrode or an electric bistoury. This is therefore an invasive method.

The article "In Situ, Real-Time Identification of Biological Tissues by Ultraviolet and Infrared Laser Desorption Ionization Mass Spectrometry" Anal. Chem. 2011, 83, 1632-40, discusses an in situ analysis method for biological tissues within the scope of diagnostics or surgical operations of diverse types of cancers. The device consists of a laser coupled with a transfer tube which is connected to a mass spectrometer via an ionization source. First, this ionization source has the drawback of damaging the molecules having a high molecular weight. Secondly, this device is bulky so that if it allows analysis in situ, it is not adapted to in-vivo analysis. Thirdly, it cannot provide the relevant information in real time.

The first object of the present invention is thus the development of a device for analyzing biological material in vivo in real time based on mass spectrometry.

According to the invention, a device for molecular analysis of biological material comprises:
 a laser, optionally assisted with an optical parametric oscillator, configured for emitting a wavelength comprised between 2.5 µm and 12 µm, said thereby configured laser being intended to ablate said biological material by ejecting charged and/or non-charged particles;
 a mass spectrometer; and
 a probe including:
  at least one first analysis fiber connected to the laser, and
  a transfer tube connected to the mass spectrometer.

Thus a miniaturized instrument adapted for in vivo analysis is thereby available.

By analysis in the sense of the invention is meant the obtaining of molecular data giving the possibility of information on the physiological condition of a patient at an instant t (diagnostic) or future instant (prognose). These molecular data may directly stem from the patient but also stem from symbiotic organisms of the patient (virus, bacterium, . . . ).

The analysis fiber is connected to an ablation laser.

As an example, the wavelength of the ablation laser may be comprised between 2.8 µm and 3.2 µm. More generally, the laser is configured for providing, optionally assisted with an optical parametric oscillator (OPO), a wavelength comprised between 2.5 µm and 12 µm.

The transfer tube is connected to a mass spectrometer.

According to an additional characteristic of the device, the laser is a pulsed laser configured for generating a beam for which the energy is comprised between 2 mJ/pulse and 15 mJ/pulse and the surface between 30 $\mu m^2$ and 3 $mm^2$.

According to an additional characteristic, a system for focussing and transferring ions is interposed between said transfer tube and the mass spectrometer.

According to another additional characteristic, a metal grid, advantageously extremely thin, is introduced between the transfer tube and the mass spectrometer.

This grid advantageously gives the possibility of increasing the sensitivity of the analysis by increasing the production of ions.

According to another additional characteristic of the invention, a nebulization capillary is connected to the depressurization capillary.

Thus, the nebulization capillary is connected to a solvent distribution means.

It may be necessary to provide a second analysis fiber.

According to the invention, the device further includes a therapy fiber for laser therapy.

Advantageously, the therapy fiber is connected to a laser with a wavelength adapted for destroying cells.

The advantage of the system is to give the possibility of combining an analysis system and that of a therapy system. According to the results obtained via the analytical part, the tissues may be processed via the therapy fiber.

According to a particular embodiment, the probe further includes an illumination channel and an image shooting channel.

This embodiment will quite particularly be suitable for endoscopic use.

The present invention will now appear in a more detailed way within the scope of the description which follows of an exemplary embodiment given as an illustration with reference to the appended figures which illustrate:

FIG. 5a shows the total ion current over the whole of the acquisition period,

FIG. 5b, illustrates the spectrum obtained during the laser irradiation period,

FIG. 6a shows the results obtained on the liver, FIG. 6b shows the results obtained on the brain.

The elements present in several figures are assigned a single and same reference.

Figure 1:
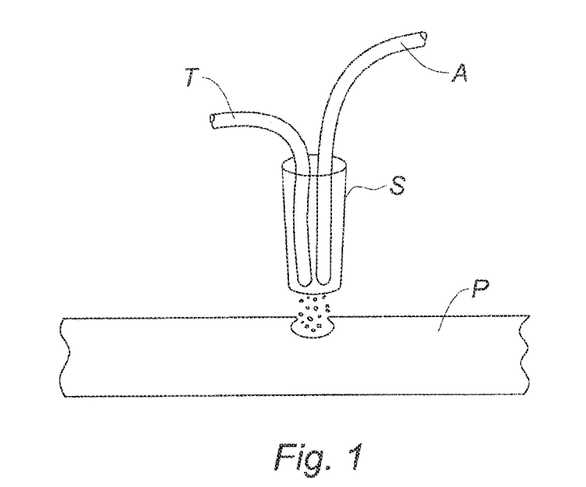
FIG. 1 shows a perspective scheme of a probe according to a first embodiment of the invention.

With reference to FIG. 1, a probe has been illustrated according to the invention in quasi-contact with a biological material to be analyzed P, the skin of a patient in this case (but this may quite also be an organ).

The probe S appears as a cylinder in which appear an analysis fiber A and a transfer tube T. Both of these elements are flushed with the front face of the probe, the one which comes in proximity to the biological material to be analyzed. The function of these elements is explained later on.

This is the embodiment at the basis of the invention which gives the possibility of carrying out an external analysis on the skin, the hair, the nails or internally on an organ during open surgery.

Figure 2:
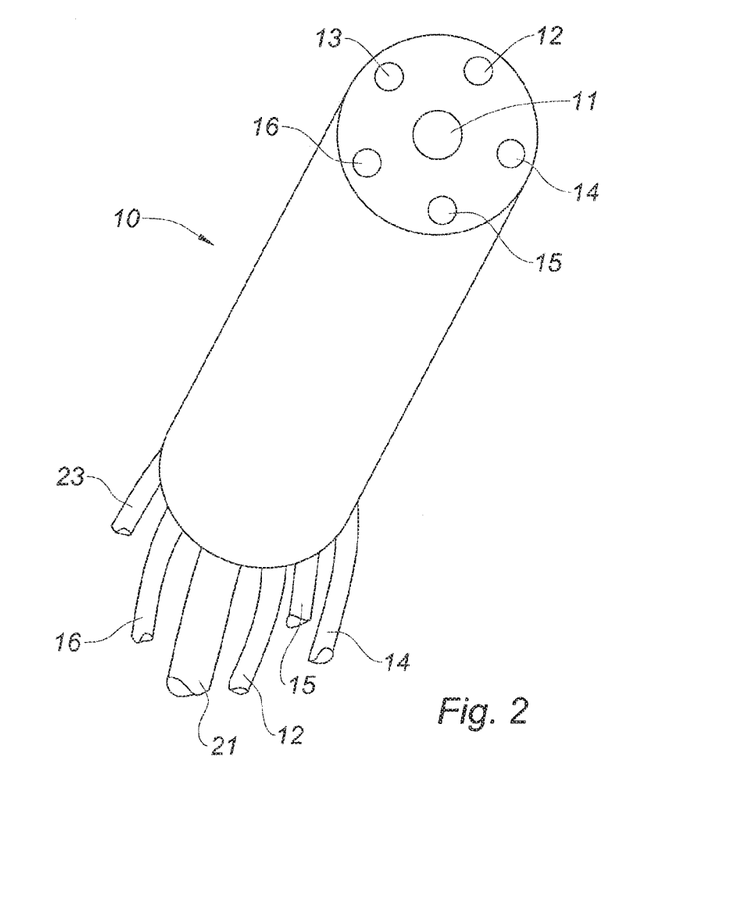
FIG. 2 shows a perspective scheme of an endoscopic probe according to the invention.

According to a development of the invention, the probe is in fact an endoscopic probe which includes additional elements.

With reference to FIG. 2, the endoscopic probe 10 appears here as a cylinder having an axial recess 11.

It has an analysis face or a front face which is visible in the figure and which also has an opposite face, the rear face which does not appear in the figure.

The actual recess 11 is also cylindrical and a transfer tube 21 is inserted therein. The function of this transfer tube is detailed further on.

In parallel with the recess 11 are placed several elements which then also are cylindrical.

First, an illumination channel 12 such as an optical fiber opens onto the rear face so as to be connected to an illumination device not shown in this figure.

Secondly, an image shooting channel 13 is positioned in proximity to the illumination channel 12. It includes an image shooting apparatus such as a camera and the output on a rear face is accomplished through a video link 23.

Thirdly, a first optical analysis fiber 14 which is flushed with the analysis face opens onto the rear face. Its connection is explained subsequently.

Advantageously, a second optical analysis fiber 15 may be provided which also opens onto the rear face.

For the case when the probe is also used for treatment by laser therapy, the latter further includes a laser therapy fiber 16 which again opens onto the rear face.

Figure 3:
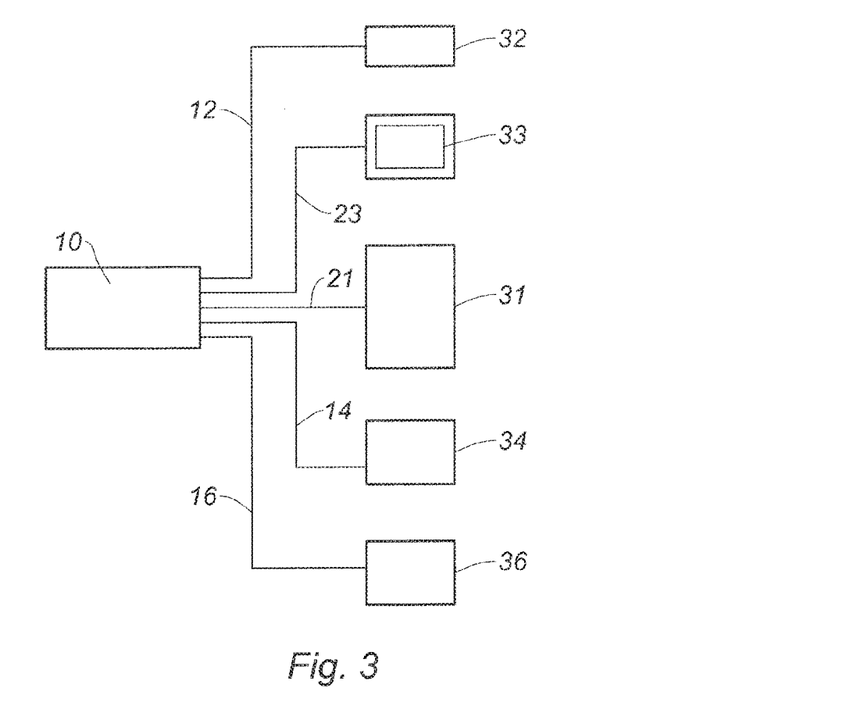
FIG. 3 shows a scheme of this probe connected to the equipment required for its application.

With reference to FIG. 3, the different connections of the probe 10 are explained.

The illumination channel 12 is connected to an illumination device 32.

The video link 23 is connected to a viewing screen 33.

The transfer tube 21 is connected to a mass spectrometer 31. The detail of this connection is provided later on.

This transfer tube preferably consists of a material aiming at minimizing the absorption phenomena in order to ensure an efficient transfer of the ablated material through the analysis fiber. This material is for example PTFE.

The first analysis fiber 14 is connected to a first ablation laser 34. This laser 34 has the function of sampling the tissue which it irradiates thereby causing ejection of charged particles (molecular ions) and/or non-charged particles in a gaseous phase.

The wavelength of this laser may be selected in the domain which extends from infrared to ultraviolet, preferentially in the infrared.

For example this is a laser with a wavelength comprised between 2.8 µm and 3.2 µm, typically an erbium-YAG laser emitting at a wavelength of 2.94 µm.

Mention may also be made of:

Neodymium-YAG lasers: 1.064 µm; 0.532 µm; 0.355 µm; 0.266 µm

Xe—Ne lasers: from 2 µm to 4 µm

HF (Hydrogen fluoride) lasers: 2.6 µm

Fiber lasers of the Ytterbium type, doped with bismuth, thulium or holmium: from 1.07 µm to 2.1 µm.

These lasers may be used as direct sources of emission or coupled with an OPO (Optical Parametric Oscillator). An OPO actually allows from a laser wave of a given wavelength to produce two waves with a larger wavelength. This therefore gives the possibility of widening the range of wavelength which may be used for the relevant laser, seen by the biological material to be ablated.

Generally, it is sought to cover the range of wavelengths from 2.5 µm to 12 µm. Indeed, in this range of wavelengths, the absorption bands of O—H, N—H, C—H, C=O, C=N, C=C, C—O, C—N and C—C bonds are covered, which may be present in the biological material to be ablated.

In particular, in this range of wavelengths from 2.5 µm to 12 µm, the laser gives the possibility of ablating the biological material by generating at least charged particles, in particular molecular ions, in a gas phase.

However it is possible to limit oneself to the range of wavelengths comprised between 2.5 µm and 3.5 µm. Indeed, in this range of wavelengths, the absorption bands of the O—H, N—H and C—H bonds are covered.

It is possible to limit oneself to a range of more limited wavelength, comprised between 2.8 µm to 3.2 µm. Indeed, in this range of wavelengths, the absorption bands of the O—H and N—H bonds are covered.

Moreover, the ablation laser 34 will advantageously be a pulsed laser configured for generating a beam for which the energy is advantageously comprised between 2 mJ/pulse and 15 mJ/pulse, the surface of the beam (focussing) being comprised between 30 µm$^2$ to 3 mm$^2$.

The energy of the beam may be comprised between 5 mJ/pulse and 12 mJ/pulse, or further between 5 mJ/pulse and 10 mJ/pulse, the surface area of the beam (focussing) being comprised between 30 µm$^2$ to 3 mm$^2$.

For the ranges of energies considered earlier, the laser beam may moreover have a surface area comprised between 100 µm$^2$ and 3 mm$^2$, between $10^{-3}$ mm$^2$ and 3 mm$^2$, between $10^{-2}$ mm$^2$ and 3 mm$^2$, between $10^{-1}$ mm$^2$ and 3 mm$^2$, between 0.5 mm$^2$ and 3 mm$^2$, or between 0.5 mm$^2$ and 2 mm$^2$. In particular, the beam of the laser may typically ablate a volume of biological material for which the base surface is of the order of the 1 mm$^2$, which substantially corresponds to a beam for which the surface area or focussing is also of the order of 1 mm$^2$.

The inventors have actually been able to ascertain that this selection in the energy provided by a pulse of the ablation laser 34 and in the surface area (focussing) of this beam ensured better production of molecular ions and therefore brought a synergistic effect with the selection of the range of wavelengths of the laser specified above.

Moreover it should be noted that the penetration depth of the laser beam is typically of a few microns per laser pulse.

If a second diagnostic fiber is provided, the latter is connected to a second ablation laser of a type different from the first. The possibilities of the diagnostic are thereby increased. Let us mention as an example the Neodymium-YAG laser at a wavelength of 0.532 µm. Let us also mention as an example also another laser, optionally coupled with an OPO for acting in the range from 2.5 µm to 3.5 µm. Said second analysis fiber advantageously giving the possibility of increasing the analysis possibilities.

The thereby ejected particles are managed by the transfer tube 21 which will forward them to the mass spectrometer 31.

The laser therapy fiber 16 is connected to a therapy laser 36. Actually, if the analysis carried out earlier reveals that the tissues have to be treated, the treatment may take place immediately, this without using any piece of additional equipment. Thus, for example it is possible to use for therapy, a laser (laser diode) emitting at 980 nm, as proposed by Gonzalez-Mertinez et al., "Robot-assisted stereoactic laser ablation in medically intractable epilepsy: operating technique, Neurosurgery, 2014, suppl 2: 167-172.

Figure 4:
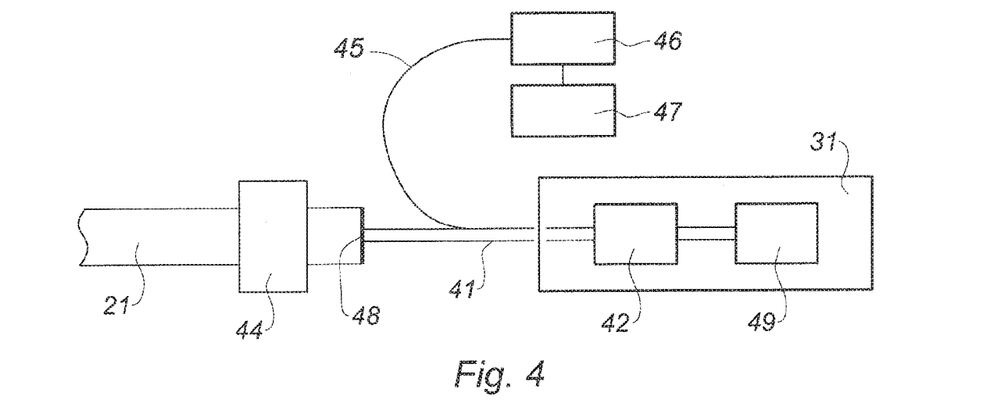
FIG. 4 shows a scheme of the transfer line which connects the probe to the mass spectrometer.

With reference to FIG. 4, a connection example is detailed between the probe 10 and the mass spectrometer 31.

The transfer tube 21 is extended with a de-pressurization capillary 41 on the opposite side to that of the probe 10. The capillary is preferably a metal capillary. It has a smaller internal diameter than that of the transfer tube 21. This gives the possibility of increasing the de-pressurization of the mass spectrometer 31, which induces an acceleration of the particles. If this capillary 41 is a metal capillary, it is possible to generate an electric field for generating a potential difference between this capillary and the inlet of the mass spectrometer 31.

The de-pressurization capillary 41 is extended at the inlet of the mass spectrometer 31 with a system for focussing and transferring ions 42 integrated inside the mass spectrometer.

Alternatively, this system 42 may be positioned outside the mass spectrometer, upstream from the latter, with reference to the path of charged or non-charged particles.

Moreover, also alternatively, this system 42 may be a system for focalizing ions or a system for transferring ions.

This system 42 gives the possibility of guiding the aerosol including charged particles or not towards the mass spectrometer.

The transfer tube 21 may be provided with a heating means 44 for increasing its temperature.

It is also possible to provide a nebulization capillary 45 which will be connected to the de-pressurization capillary 41. This nebulization capillary 45 is supplied with a distributor of solvent 46. A control member 47 is provided for regulating the distributor 46 so that the solvent flow rate is the desired one. This solvent gives the possibility of reproducing a conventional electrospray process in order to increase the production yield of charged molecules (molecular ions). The advantage of introducing the solvent in this location is the absence of toxicity both towards the users and towards biological tissues.

However, this is only proposed as an option. Also, it is possible to contemplate that no electrospray means connected to a solvent distribution means is provided between the transfer tube T, 21 and the mass spectrometer 31. Indeed, an advantage of the invention is that the ablation process of the biological material gives the possibility of ejecting at least charged particles (molecular ions) in a sufficient amount of their subsequent analysis with the mass spectrometer.

Moreover, it is also possible to provide a distribution capillary which will be connected to the de-pressurization capillary. This distribution capillary is then supplied by a gas distributor containing GH+ ions. This gives the possibility of inducing, by collision, a transfer protons to the particles to be analyzed and thereby increase the yield of the ion production. This case is not illustrated in the appended figures, but the implantation of this distribution capillary and of the gas distributor may be similar to that of the electrospray capillary 45 and to its solvent distributor 46, respectively.

However, this is only proposed as an option. Indeed, it may be contemplated that no distribution capillary connected to a gas distributor is provided between the transfer tube T, 21 and the mass spectrometer 31. Indeed and as a reminder, an advantage of the invention is that the ablation process of the biological material gives the possibility of ejecting at least charged particles (molecular ions) in a sufficient amount for their subsequent analysis by the mass spectrometer.

It is also possible to provide a metal grid 48 in the transfer line which goes from the probe 10 to the mass spectrometer 31.

This grid is for example positioned between the transfer tube 21 and the de-pressurization capillary 41, as illustrated in FIG. 4.

This is an extremely thin grid of the type of those which are used in electron microscopy. Its function is to break the particles or the aggregates of particles ejected by the ablation laser 34 so that they are finally accelerated intended for the mass spectrometer 31. This grid 48 does not break the molecules, some of them are in an ionic form in the transfer tube T, 21, but larger particles.

A mass spectrometer conventionally comprises and in the following order:
  a source
  a system for transferring and focussing ions
  at least one mass analyzer
  It also comprises a detection system.

According to a particular embodiment of the invention, the mass spectrometer does not include any source and comprises at least one system for focussing and/or transferring ions interposed between the transfer tube and said mass analyzer.

In a non-limiting way, mention may be made as examples of system for focussing and/or transferring ions, a transfer capillary, a skimmer, a focussing lens, a transfer system with multipolar fields, an ion funnel, an electrostatic lens.

The mass spectrometer may also include elements aiming at improving its performances such as for example an ion mobility system.

According to a possible embodiment, the system for focussing and transferring ions is a transfer capillary.

The spectrometer comprises a mass analyzer 49. The mass analyzer used may be of any type but should be simple (eg. Simple Magnetic Sector (B) or with double focussing (BE, EB), Quadripole (Q), Ion trap (IT), time of flight (TOF), cyclotronic ion resonance (CIR), orbitrap), combined (eg. Triple Quadripole) or hybrid (eg. Q-orbitrap, Q-TOF).

Alternatively, the mass analyzer used may be another system for separating ions (e.g. ion mobility).

Let us now tackle the contemplated strategy upon using the present invention.

The device according to the invention operates on the basis of a laser ablation process giving the possibility of sampling the biological material to be analyzed. This leads to the ejection of particles in a gas phase (either charged or not). The ablated material is delivered in real time to the mass spectrometer 31 via the transfer tube 21. Indeed, the ablation process and the ejection of particles, related to this ablation, as well as the transit time in the transfer tube are short and may be described as real time. This gives the possibility of collecting the molecular profiles (signals stemming from the analysis of the biological material corresponding to biomolecules of the types of organic compounds, amino acids, metabolites, lipids, peptides, . . . ) characteristic of the analyzed area.

Advantageously, these profiles will be compared with a data bank of molecular profiles obtained by the use of the present device, in real time allowing information to be obtained in a rapid way.

The bank of molecular data is established by using the present device in an ex-vivo way on biopsies of patients illustrating different grades and stages of the relevant pathology. A cohort of samples from healthy patients or not is also integrated into the data bank.

However it is possible to establish the data bank in another way.

According to a particular use, the surgeon will displace the probe at the surface or at the inside of the patient over the relevant biological material in order to determine whether it is located in a cancer area or not allowing him/her to rapidly contemplate a treatment for the patient and notably the areas which he/she will have to remove surgically. These areas to be removed may advantageously be removed by the therapy fiber according to a particular embodiment of the device according to the invention.

The invention gave the possibility of obtaining the following results.

Result 1: Analysis of Biological Tissues ex vivo

A laser emitting nanosecond pulses at a frequency of 10 Hz (Quantel Easy Brillant, Les Ulis, France), connected to an OPO system with a crystal of the $LiNbO_3$ (variable in wavelength between 2.5 and 4.5 μm, LaserSpec, Malonne, Belgium) adjusted to a wavelength of 2,940 nm is used. A Teflon transfer tube (inner diameter 10 mm) is used for transferring charged and non-charged particles, and is directly connected to a mass spectrometer of the ion trap type for which the source has been withdrawn (HCT Ultra, Bruker Daltonics, Bremen, Germany). The arrival of $N_2$ of the mass spectrometer was disconnected in order to allow the addition of a pump aiming at increasing the suction flow rate in the transfer tube. The analysis of the compounds stemming from laser irradiation is carried out with the mass spectrometer in a negative mode over a mass over charge (m/z) ratio range comprised between 150 and 1,000.

Figure 5:
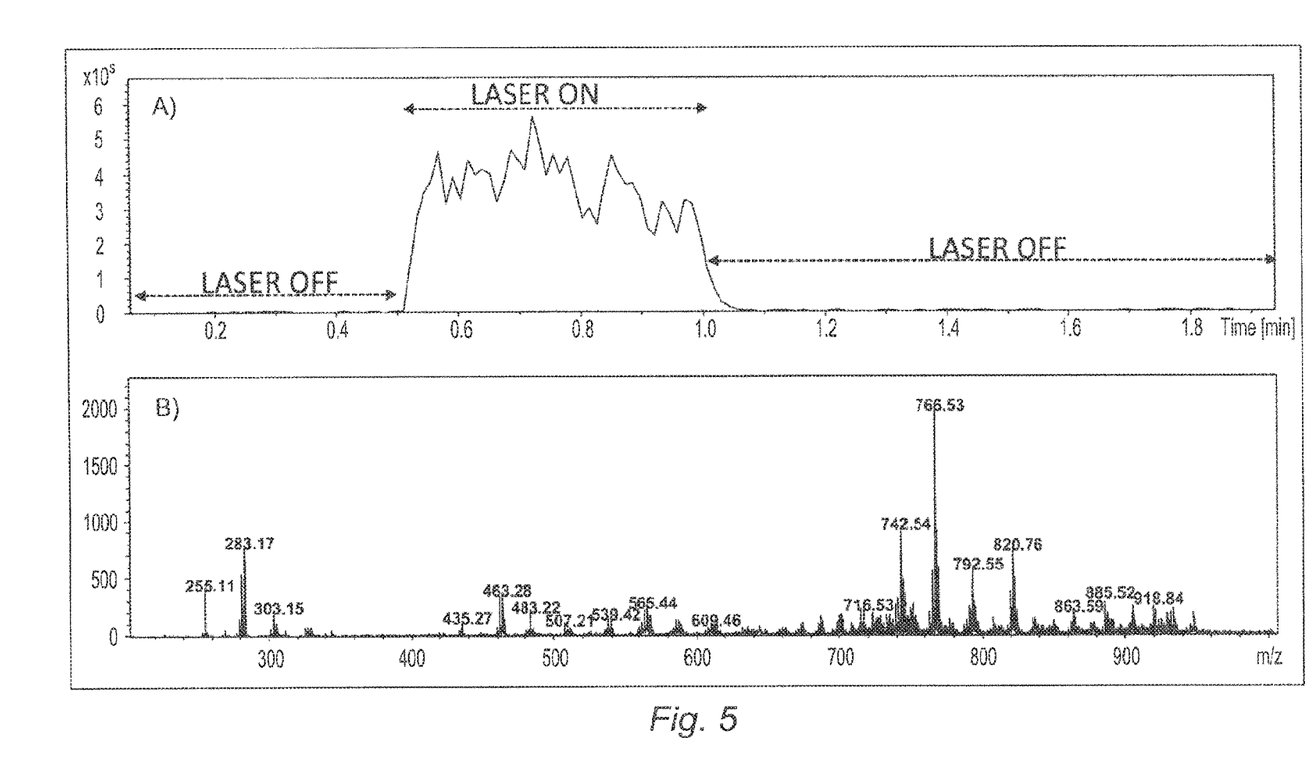
FIG. 5 shows a spectrometry diagram relative to the analysis of a biological tissue ex vivo and notably of a bovine liver, more particularly.

The first experiment shown in FIG. 5 is the analysis ex vivo of a piece of bovine liver. On the latter, an irradiation of 7 mJ/laser shot over an area of 1 mm² (1 laser shot=1 laser pulse) is achieved. A number of 3 phases was selected during the acquisition step: a first step in absence of laser irradiation, a phase with laser irradiation and another phase in the absence of laser irradiation. FIG. 5A illustrates the total ion current over the whole of the acquisition period and FIG. 5B shows the spectrum obtained during the laser irradiation period. The total ion current shows that the presence of a detected signal is in correlation with laser irradiation. Therefore, there are no compounds which adhere to the internal wall of the transfer tube and this shows a rapid analysis, in real time. Typically, the analysis time is less than 1 second.

Figure 6:
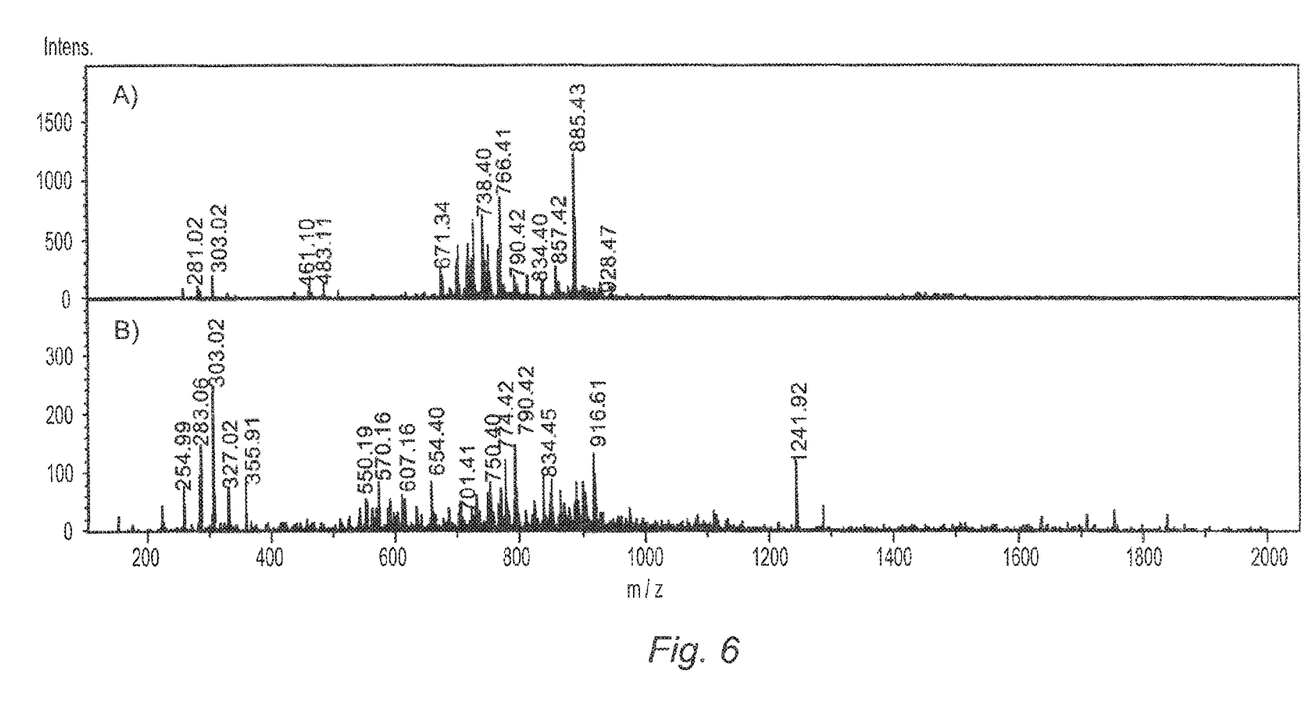
FIG. 6 shows a comparison of an ex vivo analysis between the liver and the brain of a rat, more particularly.
Figure 7:
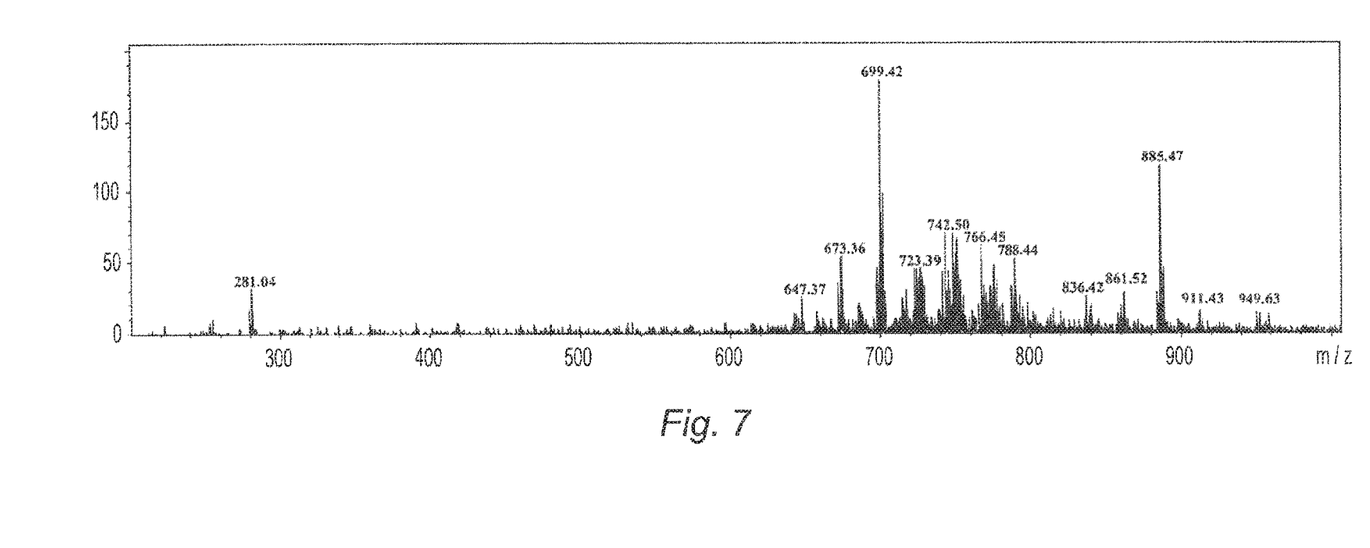
FIG. 7 shows an analysis of a cancer biopsy of a lymphoma of a dog

In FIG. 6, a comparison of 2 organs in rat, the brain and the liver is carried out on an acquisition on each organ. An irradiation of 30 seconds at 7 mJ/laser shot over a region of each organ. FIG. 6 shows a m/z ratio difference between these 2 organs which shows a specificity of molecular composition of the brain as compared with the rat liver. In FIG. 7, an analysis of a cancer biopsy of a lymphoma of dogs is carried out. An irradiation of 30 seconds at 7 mJ/laser shot is carried out over a region of this biopsy. The recorded spectrum is selected at the laser irradiation period. It shows a signal generation corresponding to lipids and to fatty acids and a few signal ascribable to peptides. The present invention gives the possibility of carrying out analysis in real time without contamination at the wall of the Teflon tube but also between different organs stemming from a same animal. The real time analysis carried out on the different organs shows a significant number of signals which may correspond to fatty acids, metabolites and lipids. With reference to FIG. 6, the present invention has the capability of detecting different profiles according to the investigated organs and to their physiological status (e.g. healthy versus carcinogenic). The advantage of this analysis is a large disparity in the families of detected molecules which may add a significant value both on the data bank of molecular profiles but also on the characterization of the biological tissues.

Result 2: Analysis of Biological Tissues in vivo

Figure 8:
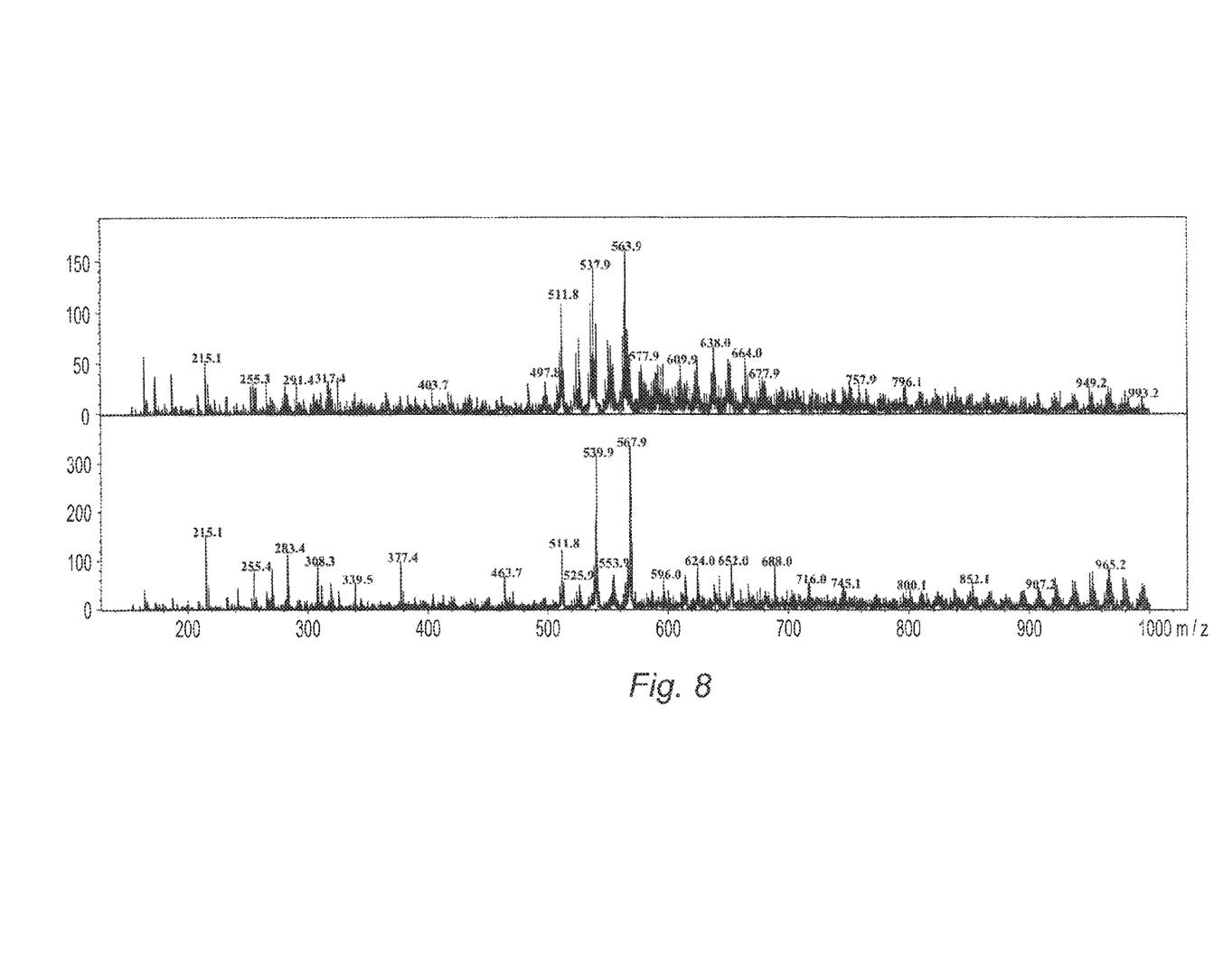
FIG. 8 shows analyses of digital imprints, a comparison man/woman (in vivo analysis on fingers).

In FIG. 8, a real time analysis in-vivo of the tissues of the skin of individuals of different gender is carried out at the fingers. An irradiation of 10 seconds at 9 mJ/laser shot (1 laser shot=1 laser pulse) for each individual is carried out by means of a laser emitting nanosecond pulses at a frequency of 10 Hz (Quantel Easy Brillant, Les Ulis, France), connected to an OPO system with a crystal of the $LiNbO_3$ type (variable in wavelength between 2.5 and 4.5 μm, LaserSpec, Malonne, Belgium) adjusted to a wavelength of 2,940 nm. A Teflon transfer tube (inner diameter 10 mm) is used for transferring either charged and non-charged particles, and is directly connected to a mass spectrometer of the ion trap type for which the source has been withdrawn (HCT Ultra, Bruker Daltonics, Bremen, Germany). The arrival of $N_2$ of the mass spectrometer was disconnected in order to allow the addition of a pump aiming at increasing the suction flow rate in the transfer tube. The analysis of the compounds stemming from laser irradiation is carried out with the mass spectrometer in a negative mode over a range of mass over charge ratio (m/z) comprised between 150 and 1,000. A number of 3 phases was selected during the acquisition step: a first phase in the absence of laser irradiation, a phase with laser irradiation and another phase in the absence of laser irradiation. A distinction of the different individuals is viewed in FIG. 8. The present invention gives the possibility of carrying out analysis in vivo in real time on individuals and to be able to observe molecular profile specific according to the gender of the individual. This analysis in vivo on individuals shows the non-invasive and painless effect of the present invention during several seconds of irradiation.

Another advantage of the present invention is the non-invasive effect on organs during the actual irradiation for several tens of seconds on a same point. Based on the molecular profile, the present invention is used for differentiation of very reduced areas (diameter of the irradiation area of 400 μm) of biological tissues.

The invention also relates to a method for molecular analysis of biological material, characterized in that it comprises the following steps:
  emitting a laser beam at a wavelength comprised between 2.5 μm and 12 μm towards a biological material, the interaction between this beam and the biological material causing the ablation of the latter and the ejection of at least charged particles, notably molecular ions;
  directing the ablated biological material including at least said charged particles towards a mass spectrometer, via a transfer tube; and
  analyzing the composition of the ablated biological material in the mass spectrometer.

This molecular analysis method of biological material may be carried out in vivo.

The laser beam may have a wavelength comprised between 2.5 µm and 3.5 µm or between 2.8 µm and 3.2 µm.

Moreover, the laser beam may be pulsed and have an energy comprised between 2 mJ/pulse and 15 mJ/pulse, the surface of the beam (focussing) being comprised between 30 µm² and 3 mm².

The energy of the beam may be comprised between 5 mJ/pulse and 12 mJ/pulse, or further between 5 mJ/pulse and 10 mJ/pulse, the surface of beam (focussing) being comprised between 30 µm² and 3 mm².

For the ranges of energies considered earlier, the laser beam may moreover have a surface area comprised between 100 µm² and 3 mm², between $10^{-3}$ mm² and 3 mm², between $10^{-2}$ mm² and 3 mm², between $10^{-1}$ mm² and 3 mm², between 0.5 mm² and 3 mm², or between 0.5 mm² and 2 mm². In particular, the beam of the laser typically gives the possibility of ablating a volume of biological material for which the base surface is of the order of the 1 mm², which substantially corresponds to a beam also of the order of 1 mm².

Further, this method may provide a step for heating the ablated biological material.

This method may also provide a step during which the ablated biological material is sifted with a grid, for example a metal grid.

Finally, it should be noted that the invention also proposes the use of a molecular analysis device according to the invention for ablating said biological material by ejecting charged and/or non-charged particles, and more specially for ablating said biological material by ejecting at least charged particles, notably molecular ions.

The invention claimed is:

1. A molecular analysis device for a biological material comprising:
   a laser configured for emitting a wavelength comprised between 2.5 µm and 12 µm, said thereby configured laser being capable of ablating said biological material by ejecting charged or non-charged particles;
   a mass spectrometer; and
   a probe including
      at least one first analysis fiber connected to the laser, and
      a transfer tube,
   the probe being a body in which the first analysis fiber and the transfer tube are at least partially contained,
   said transfer tube being connected to the mass spectrometer.

2. The device according to claim 1, wherein the laser is configured for emitting a wavelength comprised between 2.5 µm and 3.5 µm.

3. The device according to claim 1, wherein the laser is configured for emitting a wavelength comprised between 2.8 µm and 3.2 µm.

4. The device according to claim 1, wherein the laser is a pulsed laser configured for generating a beam for which energy is comprised between 2 mJ/pulse and 15 mJ/pulse and the surface of which is comprised between 30 µm2 and 3 mm2.

5. The device according to claim 4, wherein the laser is a configured for generating a beam for which the surface area is comprised between 0.5 mm2 and 2 mm2.

6. The device according to claim 5, further comprising a de-pressurization capillary inserted between said transfer tube and said focussing or transfer system, the inner diameter of this de-pressurization capillary being less than that of the transfer tube.

7. The device according to claim 6, wherein the de-pressurization capillary is a metal capillary and in that a means is provided for generating a potential difference between said de-pressurization capillary and the mass spectrometer.

8. The device according to claim 6, further comprising an electrospray capillary connected to said de-pressurization capillary and further connected to a means for distributing solvent.

9. The device according to claim 6, further comprising a distribution capillary connected to said de-pressurization capillary and further connected to a gas distributor.

10. The device according to claim 1, wherein the laser is a pulsed laser configured for generating a beam for which the energy is comprised between 5 mJ/pulse and 12 mJ/pulse, and the surface is comprised between 30 µm2 and 3 mm2.

11. The device according to claim 10, wherein the laser is a pulsed laser configured for generating a beam for which the energy is comprised between 5 mJ/pulse and 10 mJ/pulse.

12. The device according to claim 1, wherein a system for focussing or transferring molecular ions formed during ablation of biological material is interposed between said transfer tube and the mass spectrometer.

13. The device according to claim 12, wherein said focussing or transfer system is a transfer capillary.

14. The device according to claim 1, wherein said transfer tube is provided with a heating means.

15. The device according to claim 1, wherein a metal grid is introduced between said transfer tube and said mass spectrometer.

16. The device according to claim 1, is no electrospray capillary connected to a means for distributing solvent is provided between the transfer tube and the mass spectrometer.

17. The device according to claim 1, is no distribution capillary connected to a gas distributor is provided between the transfer tube and the mass spectrometer.

18. The device according to claim 1, wherein said probe includes a second analysis fiber.

19. The device according to claim 1, wherein said probe further includes a therapy fiber.

20. The device according to claim 19, wherein said therapy fiber is connected to a therapy laser.

21. The device according to claim 1, wherein said probe further includes an illumination channel and an image shooting channel.

22. The device according to claim 1, wherein said transfer tube is made of PTFE.

23. The device according to claim 1 wherein the laser is assisted with an optical parametric oscillator.

* * * * *